(12) United States Patent
Braaten

(10) Patent No.: US 7,654,162 B2
(45) Date of Patent: Feb. 2, 2010

(54) DEVICE FOR INSTALLATION OF A PROBE AND PROBE ACCOMMODATING ARRANGEMENT

(75) Inventor: Nils A. Braaten, Trondheim (NO)

(73) Assignee: Roxar ASA, Stavanger (NO)

( * ) Notice: Subject to any disclaimer, the term of this patent is extended or adjusted under 35 U.S.C. 154(b) by 378 days.

(21) Appl. No.: 11/612,664

(22) Filed: Dec. 19, 2006

(65) Prior Publication Data

US 2008/0115602 A1    May 22, 2008

(30) Foreign Application Priority Data

Nov. 20, 2006  (NO) .................................. 20065336

(51) Int. Cl.
*G01D 11/00* (2006.01)
*G01M 19/00* (2006.01)

(52) U.S. Cl. .................................... 73/866.5
(58) Field of Classification Search ................. 73/866.5
See application file for complete search history.

(56) References Cited

U.S. PATENT DOCUMENTS

| | | | |
|---|---|---|---|
| 3,589,588 A | 6/1971 | Haneline, Jr. | |
| 4,002,059 A | 1/1977 | Jeffers et al. | |
| 4,275,592 A | 6/1981 | Atwood et al. | |
| 5,303,602 A * | 4/1994 | Morgan | 73/866.5 |
| 5,770,809 A * | 6/1998 | Waterman | 73/866.5 |
| 7,472,615 B2 * | 1/2009 | Mayeaux | 73/866.5 |
| 2006/0123933 A1 | 6/2006 | Braaten | |

FOREIGN PATENT DOCUMENTS

| | | | | |
|---|---|---|---|---|
| GB | 2150061 A * | 6/1985 | | |
| GB | 2230060 A * | 10/1990 | | |
| WO | WO 9209723 A1 * | 6/1992 | | 29/700 |
| WO | 2006/118471 A1 | 11/2006 | | |

* cited by examiner

*Primary Examiner*—Thomas P Noland
(74) *Attorney, Agent, or Firm*—Dennison, Schultz & MacDonald

(57) ABSTRACT

Device for mounting and demounting of a probe to be arranged in an access tube to a process pipeline, including a hydraulic cylinder accessing the access tube with a gripping tool to engage a probe for moving this probe into an operating position in the access tube and retrieving the probe from this position. A revolving unit with at least two chambers is provided, each chamber accommodating an axially movable probe. The chambers are accessible by the gripping tool to move a probe into a chamber and, in a subsequent step, from the chamber into the access tube. A powering device is arranged for revolving the revolving unit.

6 Claims, 2 Drawing Sheets

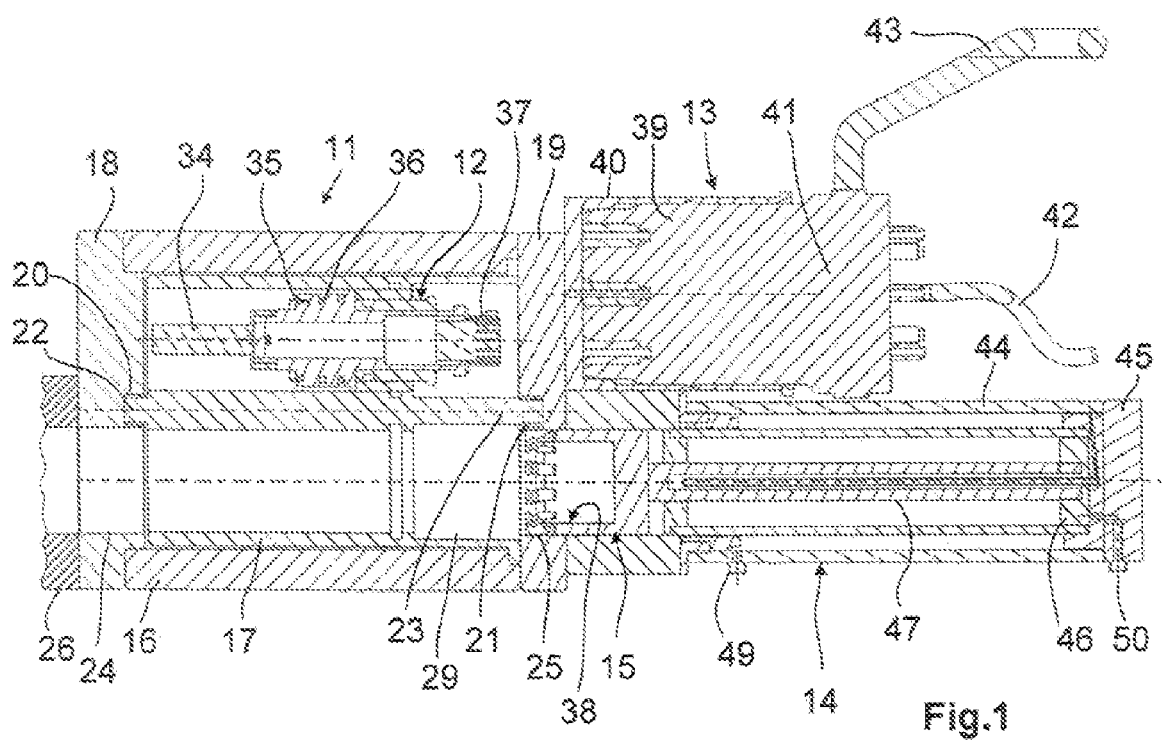

DEVICE FOR INSTALLATION OF A PROBE AND PROBE ACCOMMODATING ARRANGEMENT

BACKGROUND OF THE INVENTION

The present invention relates to a device for mounting and dismounting of a probe in process pipelines, tanks etc., as well as a probe accommodating arrangement.

Several suggestions exist for mounting and dismounting probes in process pipelines, tanks etc. Such probes are used for measuring corrosion, pressure, temperature etc, inside a system, such as in oil, gas and process industries. With a nipple, a probe can be mounted through a hole in the equipment into a tube to contact the medium of the process.

The mounting and demounting of probes is preferably conducted at normal operating conditions, which means that the system is not shut down when probes are to be changed or inspected. In connection with process a pipeline, this means that the normal operating pressure is maintained, and that draining of fluid/gas will not be necessary. This means a substantial reduction of the maintenance costs.

The disadvantage of prior art hydraulic and/or mechanical retrievers is the risk of leakage upon the mounting and demounting of the probes. This may be detrimental to the environment.

In the offshore oil industry, process pipelines and transport pipelines are placed on the sea bottom. The condition for such pipeline needs surveillance and probes have to be mounted and demounted for maintenance and upgrading. For various reasons it is desirable to use remote operated vehicles (ROVs) to conduct this operation. The depth of the sea bottom may make the use of divers dangerous and even impossible, and it is more economical to use a ROV. The security of such work has to be high, as a leakage can have large economic and environmental consequences.

Prior art technology is largely based on mechanical operations, such as use of threaded connections between a retriever and the probe and between an access tube and the retriever, and use of mechanically operated handles for opening and closing valves. Such mechanical operation can be difficult to accomplish by a ROV.

Efforts have been made to reduce the number of operations and to replace some of the threaded connections with simpler mechanisms. U.S. Pat. No. 3,589,388 (Haneline, 1971) shows a pressure operated retriever for withdrawing an injector nozzle from a high pressure environment. This structure comprises a ball valve which in its open condition has an opening for introducing the injector nozzle. Further it comprises a partly hollow or tubular connection device with two or three grooves for defining a plurality of fingers. A radially protruding tongue is arranged on each finger to be accommodated in an opening behind an injector needle. The fingers are resilient to enable connection to the opening. The probe can be pulled out by the retriever due to this connection, A disadvantage of this retriever system is the need for a screw connection radially to the access tube to fasten the injector needle. The connector device can only be pulled out of the opening without the injector needle when the screw is tightened.

U.S. Pat. No. 4,275,592 (Atwood et al, 1981) shows a retriever utilizing fingers with lips to pull a probe. A number of threaded connections are shown. This retriever will not be suitable for exchanging probes in sub-sea pipelines.

U.S. Pat. No. 4,002,059 (Jeffers et al, 1977) shows a retriever for mounting and demounting of probes with corrosion coupons in process pipelines. During operation, the probe is locked in grooves in the access tube by spring-loaded locking means on the probe. The retriever can be lowered over the probe by a wire comprising a grappling means and a rod-like body. As the retriever is lowered over the probe, the rod-like body is lowered through an opening in the upper part of the probe to release the spring-loaded locking means. The grappling means comprises arms catching a circular groove at the top of the probe, before the probe can be lifted from the access tube.

The disadvantage of this retriever is the need for two different tools for mounting and for demounting the probe. Additionally, a weight and wire are used for lowering and pulling the probe. Neither of these arrangements will be suitable for ROV operation.

From Norwegian patent specification 317390 (CorrOcean, 2004, and corresponding to U.S. Published application 2006/0123933), a device for mounting a probe in a process pipeline or a process tank is known, which device is not provided for remote operation by an ROV.

From PCT Application WO2006/1 18471 (CorrOcean 2006), a device for mounting and demounting of a probe is known, which is arranged in an access tube to a process pipeline and/or a tank. This device requires a valve housing with a ball valve with opening for handling of the probe at mounting and demounting.

SUMMARY OF THE INVENTION

The main object of the invention is to provide a device for mounting and demounting of probes, which is suitable for use with an ROV. The device should be able to remove and/or install a probe without stopping the operation, and should comprise means for operating locking means for locking the probe to the access tube in a safe and simple way.

A secure sealing between the probe and the access tube is also important. Further it is an object to provide a probe accommodating arrangement.

To achieve these and other objects, the invention is directed to a device for mounting and demounting of a probe to be arranged in an access tube to a process pipeline or in a tank, comprising an axially acting power means, particularly a hydraulic cylinder accessing the access tube with a gripping tool to engage a probe for moving this probe into an operating position in the access tube and retrieving the probe from this position, the gripping tool being provided with locking means, the device further comprising a revolving unit with at least two chambers, each for accommodating an axially movable probe, the chambers being accessible by the gripping tool to move a probe into a chamber and in a subsequent step from the chamber into the access tube, a power means being arranged for revolving the revolving unit.

The invention is further directed to a probe mounting arrangement suitable for use with such a device, to connect a probe to, and disconnect a probe from, a structure to be monitored, the device comprising a guiding funnel arranged coaxially around a connection means on the structure to be monitored by the probe, and an element mating with the guiding funnel carrying the part of the connection means to be movably connected to the mounted probe.

BRIEF DESCRIPTION OF THE DRAWINGS

Particularly favorable embodiments of the invention are described with respect to the following examples and with respect to the enclosed drawings, in which:

FIG. 1 shows an axial section through an embodiment of a device according to the invention, showing an arrangement for changing probes in a retriever device;

FIG. 2 shows a cross section through a revolving turret arrangement corresponding to FIG. 1, with a probe in the lower bore;

FIG. 5 shows an enlarged part of FIG. 4, including the probe mounting.

DESCRIPTION OF THE PREFERRED EMBODIMENTS

Figure 3:
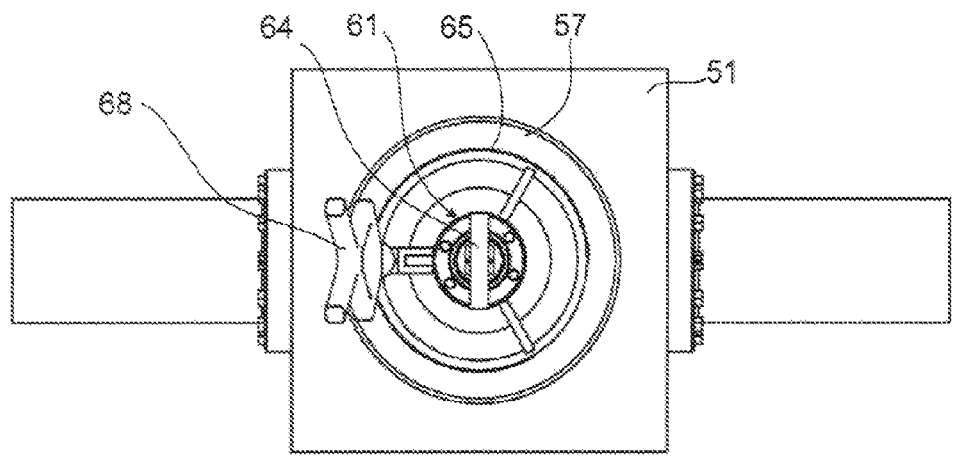
FIG. 3 shows a plan view of a connector assembly according to the invention.

FIG. 1 shows five main parts:
a turret arrangement 11, with
a probe or sensor 12;
a valve 13 for revolving the turret arrangement 11; and
a retrieving cylinder 14, with
a retrieving head 15.

Figure 4:
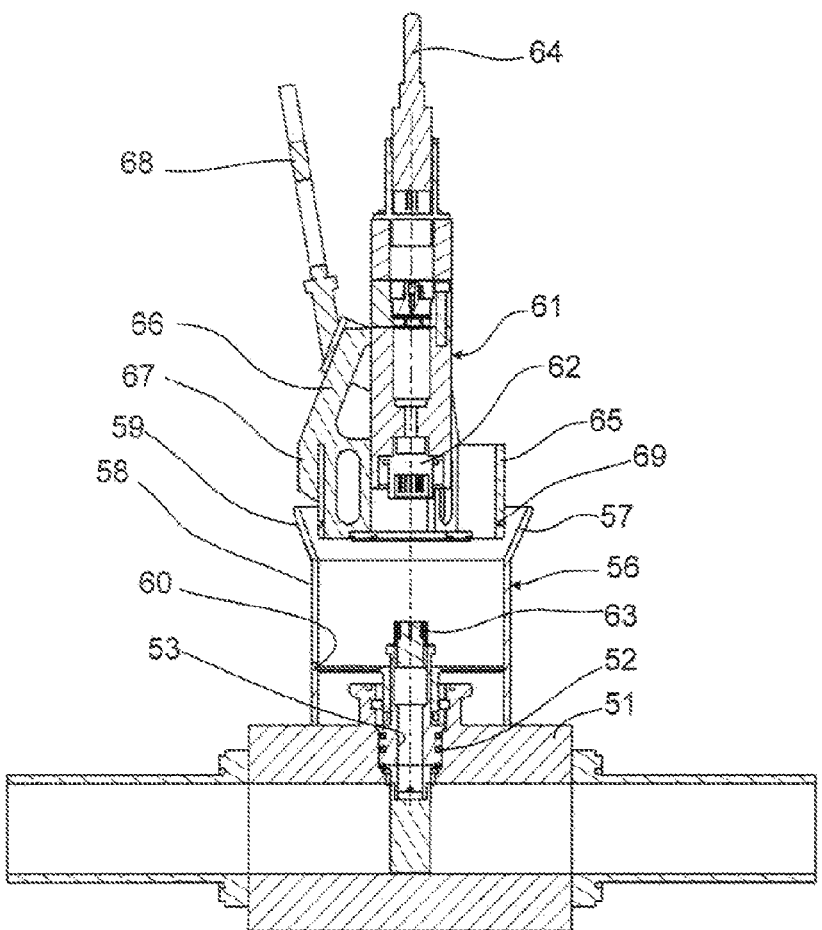
FIG. 4 shows an axial cross section of the sensor mounted on a guiding tube, with handle for ROV-operation, together with an axial cross section of the guiding funnel arranged on a fundament which is integrated with a structure to be monitored.

The turret arrangement 11 comprises a cylindrical housing 16 with a turret unit 17 inside. The cylindrical housing 16 is closed by an inner head 18 and an outer head 19, each having a central bore 20, 21 for a shaft stub 22, 23 of the turret unit 17. The housing heads 18 and 19 have axially aligned circular openings 24, 25 for passing a probe 12 through the turret unit 17. The openings 24, 25 are further axially aligned with a tubular bushing 26 provided for releasable mounting on a structure to be monitored. An example of an embodiment of such a structure will be described in connection with FIGS. 3-5 showing a connector assembly to be operated by an ROV.

The turret unit 17 has two symmetrically arranged bores 27, 28 for accommodating a probe 12. The bores 27, 28 can be axially aligned with the openings 24, 25 in the housing heads 18,19 by revolving the turret unit 17. The outer part 29 of each bore 27, 28 is enlarged with a larger diameter to accommodate a gripping device described below.

The rotation of the turret unit 17 is operated by a hydraulic motor provided by a protruding foil 30 acting as a piston in a circumferential groove 31 enclosing 180° of the circumference of the turret unit. At each end of this groove 31, a combined inlet and outlet 32, 33 is arranged with connection to the revolving valve 13.

The probe or sensor 12 is designed according to prior art, with an operating probe element 34 carried by a generally cylindrical body 35 with sealing rings 36 and with a protruding shaft 37 arranged for engagement by a mating gripping head 38 connected to the retrieving cylinder 14 as described below.

The valve 13 comprises a hydraulic valve element 39 arranged in a tubular housing 40, with a remotely controlled activator 41. The valve 13 is connected to a supply line 42 for hydraulic fluid.

The activator 41 is connected to a handle 43 for being handled by an ROV.

The retrieving cylinder 14 has an outer tubular housing 44 with an outer head 45 and a piston 46 carrying a tubular piston rod 47. The piston rod 47 carries the retrieving head 15 at the end facing the turret arrangement 11, the retrieving head being designed according to prior art to catch and move the protruding shaft 37 of a probe 12.

The tubular housing 44 is provided with inlets 49, 50 for hydraulic fluid.

In FIGS. 3-5, an embodiment of a probe connector assembly is shown. The assembly is based on a fundament 51 integrated with the structure to be monitored, e.g. a process pipeline. Access to the inside of the structure is through a bore 52.

A probe 53 is arranged in the bore 52, with sealing rings and an annular series of locking dogs 54 arranged for release with a locking bushing 55 which is slidable on the probe 53. The structure and operation of the dogs may be according to the prior art.

The fundament 51 carries a tubular funnel 56 with an upper diverging collar 57 for guiding the connector assembly to be engaged into the funnel 56. An axial slot 58 extends from a V-notch 59 in the diverging collar 57, down to the lower third of the funnel 56. Below the end of the axial slot 58 an inner groove 60 provides a recess for a sealing ring to be described below.

The connector assembly of this embodiment comprises a central housing 61 for hardware included in the connection circuit, with a lower female connector element 62 for connection with the corresponding male connector element 63 at the end of the probe 53.

The outer end of the central housing 61 is extended by a handle 64 for ROV operation.

The central housing 61 carries a coaxial guiding tube 65 mating with the inner side of the guiding funnel 56, these parts being connected with an axial arm 66. The axial arm 66 has an extension with a protruding tab 67 mating with the slot 58 to be guided by this. The arm 66 is also connected to a ROV-handle 68.

At the lower end of the guiding tube 65, a sealing ring 69 is arranged in a corresponding groove. In the mounted position of the connector assembly, the sealing ring 69 will mate with the groove in the guiding funnel 56.

A first passage 70 is arranged to extend from the inner part of this bore 52 to the outside of the fundament 51 for monitoring the pressure of the pipeline. A second passage 71 is arranged from the part of the bore 52 between the inner and the next sealing ring, for connection to a monitoring system which is provided to detect leakages in the sealing system.

The probe installation arrangement of FIGS. 3-5 is particularly advantageous in connection with a device according to the invention. This arrangement can, however, also be adapted for use with other systems for exchange of probes.

What is claimed is:

1. Device for mounting and demounting of a probe to be arranged in an access tube to a process pipeline or in a tank, comprising:
   a gripping tool for engaging the probe,
   a hydraulic cylinder for axially moving the gripping tool, the gripping tool accessing the access tube to engage the probe for moving the probe into an operating position in the access tube and removing the probe from the operating position, the gripping tool being provided with locking means,
   a revolving unit with at least two chambers, each said chamber accommodating an axially movable probe, said chambers being accessible by the gripping tool to move a probe into a chamber and in a subsequent step from said chamber into the access tube, and
   a powering device arranged for causing revolving of the revolving unit.

2. Device according to claim 1, wherein the revolving unit is arranged in a cylindrical chamber, with an axle journalled by opposite heads of the cylindrical chamber, the revolving unit comprising a pair of axial bores which are symmetrically arranged in the revolving unit, providing said two chambers.

3. Device according to claim 2, wherein the revolving unit is surrounded over a portion thereof by a circumferential groove for a wing-shaped piston to be operated by hydraulic fluid with inlets at ends of the groove.

4. Device according to claim 1, wherein the chambers for the axially movable probe are aligned in one rotational position with a central longitudinal axis of the hydraulic cylinder, and with the access tube.

5. Device according to claim 1, wherein the revolving unit is arranged in a cylindrical chamber, and the hydraulic cylinder is arranged at a free end of the cylindrical chamber, the hydraulic cylinder comprising a piston and a piston rod which carries the gripping tool in alignment with an adjacent opening in one head of the cylindrical chamber, the cylindrical chamber being entered through the opening.

6. Device according to claim 5, wherein a bore is provided in the piston rod for entry of hydraulic fluid to operate the gripping tool.

* * * * *